United States Patent [19]

Keinan

[11] Patent Number: 5,274,092
[45] Date of Patent: Dec. 28, 1993

[54] DERIVATIVES OF TRICYCLOQUINAZOLINE AND METHODS FOR THEIR PREPARATION

[75] Inventor: Ehud Keinan, Timrat, Israel

[73] Assignee: Technion Research & Development Foundation Ltd., Haifa, Israel

[21] Appl. No.: 912,834

[22] Filed: Jul. 13, 1992

[30] Foreign Application Priority Data

Jul. 14, 1991 [IL] Israel ......................................... 98824

[51] Int. Cl.$^5$ ........................................... C07D 487/16
[52] U.S. Cl. .................................. 544/245; 548/241; 560/30; 568/424; 568/442
[58] Field of Search ........................................ 544/245

[56] References Cited

PUBLICATIONS

R. W. Baldwin, et al., "Studies of the Carcinogenic Actions of Tricycloquinazoline", Brit. *Journal Cancer*, 13, 1959, pp. 94–98.
R. W. Baldwin, et al., "Studies on Tricycloquinazoline Carcinogenesis: Interaction of Carcinogen With Skin Components", Brit. *Journal Cancer*, 16, 1962, pp. 740–748.
R. W. Baldwin, et al., "Further Studies on the Influence of Peripheral Ring Substitution on the Carcinogenicity of Tricycloquinazoline", *Biochemical Pharmacologly*, 1965, vol. 14, pp. 323–331.
Fumio Yoneda, et al., "A Novel One–Step Synthesis of Tricycloquinazolines", *Chem. Pharm. Bull.* 21, (1973) pp. 1610–11611.
K. Butler, et al., *J. Chem. Soc.* "Cyclic Amidines Part IX. Tricycloquinazoline", pp. 2396–2400, (1959).
Keinan et al., *Liquid Crystals* 11, pp. 157–173 (Feb. 1992).

*Primary Examiner*—Emily Bernhardt
*Attorney, Agent, or Firm*—McAulay Fisher Nissen Goldberg & Kiel

[57] ABSTRACT

Novel discogens based on tricycloquinazoline derivatives and methods for their preparation are described. One method for their preparation is to nitrate veratraldehyde and after reducing the resulting nitrate to dimethoxy anthranil to obtain its trimerization thus producing a trisubstituted tricycloquinazoline. Another method is to start with dichlorotoluene and after its nitration to oxidize the nitrate into dichloronitrodiacetoxytoluene, its hydrolysis into benzaldehyde followed by a partial reduction to anthranil and finally by the trimerization of the anthranil to obtain the hexachlorotricycloquinazoline. The novel compounds are useful as fluorescent indicators for high performance oxygen sensors, organic conductors, liquid crystals and polymeric liquid crystals.

7 Claims, No Drawings

DERIVATIVES OF TRICYCLOQUINAZOLINE AND METHODS FOR THEIR PREPARATION

The present invention relates to new discogens based on large polycyclic aromatic cores. More particularly, the invention relates to new discogens based on tricycloquinazoline (hereinafter referred to as TCQ) derivatives and methods for their preparations.

BACKGROUND OF THE INVENTION

Discotic mesogens comprise an aromatic polycyclic core and a ring of aliphatic side chains that are connected to the core by certain functionality, e.g. by an ether linkage, ester linkage, etc.. Generally, polymethoxyarenes are common starting materials for the synthesis of such discogens due to their aryl methyl etheric groups which are cleaved to the corresponding phenols and further can be easily alkylated or acylated. As known, TCQ is readily formed by a pyrolytic reaction of various anthranilic acid derivatives. It is mentioned in the prior art that it can be obtained by the combustion of methyl anthranilate. Some review on the carcinogenic activity of TCQ were published in the Brit. Journal Cancer by Baldwin et. al. (13, p.94, 1959;16, p.740, 1962; 14, p.323, 1965). This could be explained by its high tendency for DNA intercalation, as reflected by significant stacking and aggregation in solution, its high melting point and its crystal structure. In a communication by Yoneda et al (Chem. Pharm. Bull. 21, p. 1610-1611, 1973) it is described an attempt for the preparation of three derivatives of TCQ by trimerization of an appropriate substituted anthranil derivative. TCQ is characterized by its very high thermal stability, chemical stability and high resistance to oxidation and to its coupling with diazonium salts as mentioned by Butler et al., J. Chem. Soc. p. 2396, 1959. This is a result of its highly electron-deficient benzene rings. TCQ derivatives could be expected to lead to formation of liquid crystals as a result of the increase in the core-core attractive interactions which would encourage molecular stacking. However, up to now no reports can be found in the prior art how to obtain such derivatives. It is an object of the present invention to provide new tricycloquinazolin (TCQ) derivatives and method for their preparation. It is another object of the present invention to provide new TCQ derivatives which are useful in many fields.

BRIEF DESCRIPTION OF THE INVENTION

The invention relates to new 2,6,10-trisubstituted tricycloquinazoline (I) and 2,3,6,7,10,11-hexasubstituted tricycloquinazoline (II) having the general formula:

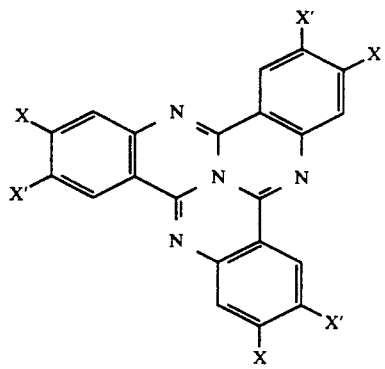

Wherein:

I) X'=H, X=SR, OR OCOR

II) X=X'=SR, OR, OCOR, —OCH$_2$C-H$_2$O—R=C$_n$H$_{2n+2}$ (n=1-18) The above new TCQ derivatives can be used for many purposes such as: fluorescent indicators for high performance oxygen sensors, organic conductors by either electrochemical crystallization or by co-crystallization with an appropriate acceptor molecule, liquid crystals components (either polymeric or monomeric liquid crystals.) The new compounds were found to be liquid crystals within a very broad temperature range. The characterization of the new mesophases was carried out by differential scanning calorimetry (DSC), optical microscopy with polarized light and X-ray diffraction. Microscopy analyses with polarized light suggested that all mesophases are hexagonal discotic, fact which was also confirmed by X-ray studies. One approach to obtain the above compounds is to start with veratraldehyde, which was easily nitrated in high yields and further reduced to the corresponding dimethoxy anthranil. Trimerization of the latter produced the 3,4,6,7,10,11-hexamethoxy TCQ in high yields. The schematic preparation is illustrated below (Scheme A):

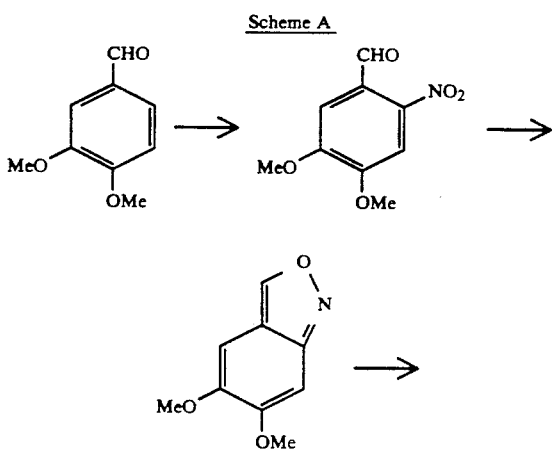

-continued
Scheme A

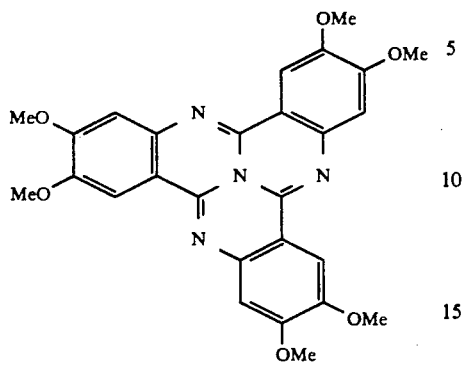

According to another approach, the starting material is selected from polyhalo-TCQ derivatives such as 2,6,10-trichlorotricycloquinazoline and 2,3,6,7,10,11 hexachlorotricycloquinazoline, as well as the corresponding tri-and hexabromo analogs. The tribromo analog, was prepared by bromination of 2-nitrotoluene; by a further oxidation with $CrO_3$ in acetic acid the 4-bromo-2-nitro-o,o-diaceto-xytoluene was obtained. The corresponding aldehyde was produced by hydrolysis with HCl. A partial reduction of the nitro derivative yielded 4-bromoanthranil which was successfully trimerized with ammonium acetate in sulfolane to yield the desired trisubstituted TCQ. The preparation of the hexa-chloro TCQ-derivative was carried out in analogy to the above. A schematic preparation is presented below (Scheme B).

-continued
Scheme B

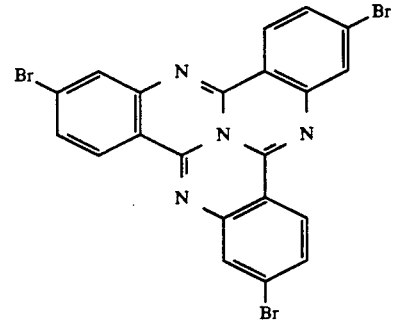

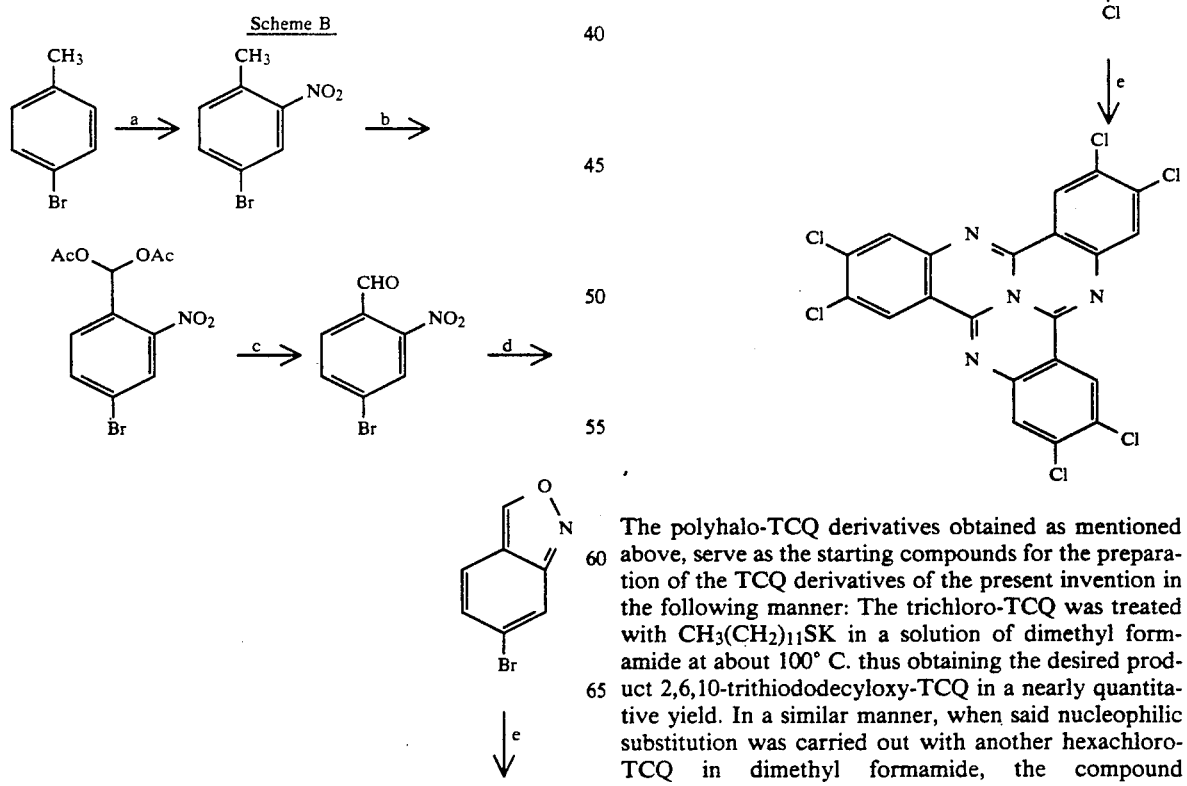

The polyhalo-TCQ derivatives obtained as mentioned above, serve as the starting compounds for the preparation of the TCQ derivatives of the present invention in the following manner: The trichloro-TCQ was treated with $CH_3(CH_2)_{11}SK$ in a solution of dimethyl formamide at about 100° C. thus obtaining the desired product 2,6,10-trithiododecyloxy-TCQ in a nearly quantitative yield. In a similar manner, when said nucleophilic substitution was carried out with another hexachloro-TCQ in dimethyl formamide, the compound 2,3,6,7,10,11-hexathiododecyloxy-TCQ was obtained. The products obtained can be easily purified by column chromatography on silica gel, followed by recrystallization from hexane. The heteroaromatic structure of these compounds are characterized by their high chemical reactivity with respect to substitution, which may be explained by the electron deficiency and electron rich perifery. The new compounds possess a very strong tendency to aggregate, even at high dilution, as was found by their $^1$H NMR spectra which are very dependent on concentration and temperature. The invention will be hereinafter described by a number of Examples, being clearly understood that these Examples are presented only for a better understanding of the invention without being limiting thereof. The following remarks are given in respect to the analyses which were carried out on the compounds prepared and the reagents used in the Examples presented below.

Infrared spectra were measured in chloroform solutions with either a Perkin-Elmer 467 grating spectrophotometer or an FT infrared Nicolet MX-1 spectrometer, and are given in cm$^{-1}$.

The NMR spectra were measured in deuteriochloroform on a Bruker ACE-200 or Bruker AM-400 NMR spectrometers. All chemical shifts are reported in o units downfield from Me$_4$Si, and the J values are given in Hertz. Splitting patterns are designated as follows: s, singlet; d, doublet; t, triplet; q, quartet; m, multiplet; br, broad.

Optical rotations were measured by a JASCO DIP 370 polarimeter, using a one decimeter cell.

High-resolution mass spectra were determined on a Varian 711 spectrometer.

Thin-layer chromatography (TLC) was performed on aluminum sheets precoated with silica gel (produced by Merck, Kieselgel 60, F254, Art. 5549).

Column chromatographic separations were performed on silica gel (Merck, Kieselgel 60, 230-400 mesh, Art. 9385) under pressure of 0.4 mm (flash chromatography).

Preparative TLC was performed on glass plates precoated with silica gel (Merck, Kieselgel 60 F-254, Art. 5717).

Distillations were performed with a Buchi kugelrohr apparatus, the temperatures noted being pot temperatures.

The tetrahydrofuran used was dried by distillation over sodium benzophenone ketyl. Methylene chloride was dried by distillation over phosphorus pentoxide, dimethyl formamide by distillation from barium oxide, and dimethyl sulfoxide by distillation over calcium hydride under reduced pressures. X-ray diffraction measurements were performed using an Elliott GX6 rotating anode generator operating at approximately 1.2 kW with a 200 um focus, to which was affixed a Searle camera equipped with Franks mirror optics.

EXAMPLE 1

Preparation of 2,6,10-tribromotricycloquinazoline

Ab amount of 11.0 g of bromoanthranil (prepared as mentioned under scheme B above) was mixed with 125 ml of sulfolane, 60 ml of acetic acid and 25 g of ammonium acetate. The mixture was stirred at 150° C. for about 16 hours, cooled to room temperature and the resultant yellow solid was collected by filtration, washed with ethanol and dried under vacuum producing crude 2,6,10-tribromo TCQ having a melting point of above 300° C.

EXAMPLE 2

Preparation of 2,3,6,7,10,11-Hexachlorotricycloquinazoline

An amount of 200 mg of dichloroanthranil (prepared as mentioned under scheme B above) and 600 mg of ammonium acetate were added to a mixture of 5 ml of sulfolane and 2 ml of acetic acid. The mixture was stirred at 140°-150° C. for 7 hours and then cooled to room temperature. The resultant yellow solid was collected by filtration, washed with water and dried under vacuum to give 74.7 mg of the 2,3,6,7,10,11-Hexachloro TCQ product. The product was highly insoluble having a melting point of above 300° C.

EXAMPLE 3

Preparation of 2,6,10-Tristhiododecyloxytricycloquinazoline

An amount of 0.30 g of potassium t-butoxide was mixed with 25 ml of dry dimethyl formamide at room temperature. To the resulted mixture, an amount of 0.6 ml of dodecanethiol was added and then the mixture was heated to about 110° C. under an argon atmosphere. To the resulted hot mixture, 0.10 g of tribromotricycloquinazoline were added which within 15 minutes at this temperature became homogeneous. The mixture was stirred for an additional two hours and then cooled to room temperature and poured into 75 ml of water. The resultant yellow precipitate was collected by filtration, washed with water and dried in vacuo. It was further purified by column chromatography (ethyl acetate:hexane) producing 95 mg of the desired product in the form of a yellow solid. The analysis by NMR shows the following:

$^1$H NMR (CDCl$_3$): 8.22 (d, J=8.5, 3H), 7.23 (d, J=1.7, #H), 7.13 (dd, J=8.5, 1.7, 3H), 3.03 (t, J=7.3, 6H), 1.74 (m, 6H), 1.53 (m, 6H), 1.26 (bd, 48H), 0.89 (q, J=3.6).

EXAMPLE 4

Preparation of 2,,3,6,7,10,11-hexa(thioalkoxy)tricycloquinazoline, when n in the the alkoxy group is 4 (using the Scheme A)

An amount of 8 ml n-thiobutanol and 3.5 g of t-butoxide were dissolved in 50 ml of dry N-methylpyrrolidinone (freshly dried on a basic alumina column) under an argon atmosphere. The reaction mixture was heated to 100° C. and then 0.45 of hexachlorotricycloquinazoline were added. The mixture was stirred for about 30 minutes, excess of 1-iodobutane was added and the mixture was allowed to cool at room temperature. The mixture was poured into a solution of 100 ml HCl (2M) and extracted with an equal volume of ether. The ether layer was washed with two portions of 50 ml of HCl (2M) followed by washing with water and dried under reduced pressure (70° C./1.5 mm Hg). obtaining a yellow-orange solid that was subjected to a column chromatography on silica gel. The column was first washed with 2.5 l of hexane in order to remove trace of solvents and non-polar by-products. The desired product was eluted with ethyl acetate-hexane (7:10) and recrystallized from boiling hexane to yield 63 mg of the desired product in the form of of an orange solid.

The analysis of the product by NMR shows the following:

$^1$H NMR (CDCL$_3$): 8.22 (s, 3H), 7.15 (s, 3H), 3.07 (t, J=7.3, 6H), 3.06 (t, J=7.2, 6H), 1.80 (m, 12H), 1.70 (m, 12H), 1.03 (q, J=7.3, 9H), 1.01 (q, J=7.3, 9H).

EXAMPLE 5

Preparation of 2,3,6,7,10,11-hexa(thioalkoxy)tricycloquinazoline, when n in the alkoxy group is 8 (using scheme B)

An amount of 2.5 g of n-thioctanol was added to 20 ml of dry N-methyl-pyrrolidinone under a nitrogen atmosphere. To this solution, an amount of 1.9 g of potassium-t-butoxide was added and the mixture was stirred for 10 minutes at 100° C. To this mixture, 200 mg of hexachlorotricycloquinazoline were added and the mixture stirred for about 20 minutes at 100° C., cooled to room temperature and worked up with water and ether. The ether extract was washed with water, dried over sodium sulfate and the solvent removed under reduced pressure. The crude product was passed on a chromatography column filled with neutral alumina (hexane-ethyl acetate 95:5) and then recrystallized from hexane-ethyl acetate, thus obtaining 254 of the desired product in the form of yellow-orange crystals. The analysis of the product by NMR shows the following:

$^1$HNMR: 8.10 (s, 3H); 7.12 (s, 3H); 3.03 (t, J=7.0 Hz, 2H); 1.76 (m,12H); 1.27 (br s, 108H); 0.84 (t, J=6.1 Hz, 18H). The present invention also includes the TCQ derivative, 2,3,6,7,10,11-hexa(thiohexoxy)tricycloquinazoline.

I claim:

1. 2,6,10-trisubstitutedtricycloquinazolines (I) and 2,3,6,7,10,11-hexasubstitutedtricycloquinazolines (II) having the formulas:

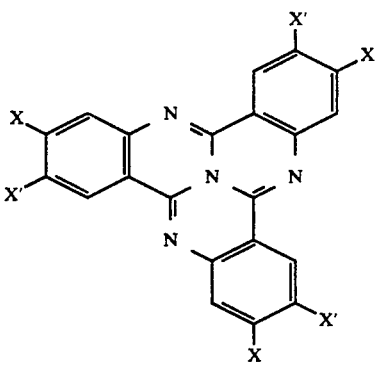

Wherein:
I) X'=H, X=SR, OR, OCOR
II) X=X'=SR, OR, OCOR, —OCH$_2$CH$_2$O—R=C$_n$H$_{2n+2}$ (n=1–18).

2. 2,6,10-tribromotricycloquinazoline.
3. 2,3,6,7,10,11-hexachlorotricycloquinazoline.
4. 2,6,10-tristhioalkyloxytricycloquinazoline wherein the alkyl is C$_n$H$_{2n+2}$ with n being from 1 to 18.
5. 2,3,6,7,10,11-hexa(thioalkyloxy)tricycloquinazoline wherein the alkyl is C$_n$H$_{2n+2}$ with n being from 1 to 18.
6. 2,3,6,7,10,11-hexa(thiohexoxy)tricycloquinazoline.
7. 2,3,6,7,10,11-hexa(thiooctoxy)tricycloquinazoline.

* * * * *